US007749955B2

(12) United States Patent
Hansen et al.

(10) Patent No.: US 7,749,955 B2
(45) Date of Patent: Jul. 6, 2010

(54) SEPARATION OF POLYPEPTIDES COMPRISING A RACEMIZED AMINO ACID

(75) Inventors: Thomas Budde Hansen, Københaven N (DK); Steffen Kidal, Københaven F (DK); Camilla Kornbeck, Birkerød (DK)

(73) Assignee: Novo Nordisk A/S, Bagsvaerd (DK)

( * ) Notice: Subject to any disclaimer, the term of this patent is extended or adjusted under 35 U.S.C. 154(b) by 548 days.

(21) Appl. No.: 11/358,676

(22) Filed: Feb. 21, 2006

(65) Prior Publication Data
US 2006/0183669 A1    Aug. 17, 2006

Related U.S. Application Data

(63) Continuation of application No. PCT/DK2004/000542, filed on Aug. 18, 2004.

(60) Provisional application No. 60/498,250, filed on Aug. 27, 2003.

(30) Foreign Application Priority Data

Aug. 21, 2003   (DK)   .................... PA 2003 01196

(51) Int. Cl.
*A61K 38/00* (2006.01)
(52) U.S. Cl. .................. 514/2; 514/3; 514/12; 530/303
(58) Field of Classification Search ........................ None
See application file for complete search history.

(56) References Cited

U.S. PATENT DOCUMENTS

| | | | |
|---|---|---|---|
| 3,907,676 | A | 9/1975 | Jorgensen |
| 4,129,560 | A | 12/1978 | Zoltobrocki |
| 4,361,510 | A | 11/1982 | Mitra |
| 5,101,013 | A | 3/1992 | Dörschug et al. |
| 5,344,918 | A | 9/1994 | Dazey et al. |
| 5,606,031 | A | 2/1997 | Lile et al. |
| 6,113,911 | A | 9/2000 | Binz et al. |
| 6,268,343 | B1 | 7/2001 | Knudsen et al. |
| 2003/0027996 | A1 | 2/2003 | Staby |
| 2003/0103980 | A1 | 6/2003 | Korc et al. |

FOREIGN PATENT DOCUMENTS

| | | |
|---|---|---|
| EP | 0207727 | 1/1987 |
| EP | 0699686 | 3/1996 |
| EP | 0708179 | 4/1996 |
| EP | 0849277 | 6/1998 |
| JP | 64-86896 | 3/1989 |
| JP | 8-337600 | 12/1996 |
| JP | 10-059866 | 3/1998 |
| JP | 10-059867 | 3/1998 |
| JP | 2000-605629 | 3/2000 |
| WO | WO 87/06941 | 11/1987 |
| WO | WO 90/00176 | 1/1990 |
| WO | WO 90/00177 | 1/1990 |
| WO | WO 90/11296 | 10/1990 |
| WO | WO 91/11457 | 8/1991 |
| WO | WO 96/32414 | 10/1996 |
| WO | WO 98/08871 | 8/1997 |
| WO | WO 98/08872 | 3/1998 |
| WO | 00/55203 | 3/2000 |
| WO | WO 00/55203 | * 9/2000 |
| WO | WO 0055203 | 9/2000 |

OTHER PUBLICATIONS

Senderoff et al., J. of Pharm. Sci., 1998, vol. 87, No. 2, pp. 183-189.*
Seneroff et.al., J. of Pharm Sci., 1998, vol. 87, No. 2, pp. 183-189.*
Stuber, W et al—Int J Peptide Protein Res—1983—vol. 22—pp. 277-283.
Senderoff, R et al—J Pharm Sci—1998—vol. 87—Part 2—pp. 183-189.
Bjorn, S. et al., Research Disclosure, vol. 9, p. 26960 (1986).
English Language Machine Translation of Japanese Patent Publication JP8337600, published Dec. 24, 1996.
Kagaku et al., Activation of Coagulation of Factor VII to VIIa Research Disclosure, pp. 564-565 (Sep. 1986).
Ohboshi et al., "Molecular Forms of Immunoreactive Glucagon-like peptide-1 (GLP-1) in Plasma," Biomedical Research, vol. 9 (Suppl. 3), pp. 47-51 (1998).
Abstract of European Patent EP 0849277; "Process for preparation of insulin by high pressure liquid chromatography."
Machine Translation of Japanese Patent JP 10059866; "Preparation of blood coagulation factor VII and/or activated blood coagulation factor VII-by developing solution containing factor VII with anion exchange resin."
Machine Translation of Japanese Patent JP 10059867; "Activation of Blood coagulation Factor VII-by ion exchange purification of a solution containing Factor VII."
Brange et al., "Chemical stability of insulin" 5. Isolation, characterization and identification of insulin transformation Acta Pharm. Nord., vol. 4, No. 4, pp. 223-232 (1992).
Dizdaroglu et al., "Separation of Peptides by Hight Performance Liquid Chromatography On A Weak Anion Exchange Bonded Phase" Journal of Chromatography, vol. 237, pp. 417-428 (1982).
Huskins et al., "Halibut Muscle 3-Phosphoglycerate Kinase. Chemical and Physical Properties of the Enzyme and Its Subtract Complexes" Biochemestry, vol. 21 pp. 4180-4189 (1982).
Kreymann et al., "Isolation and characterisation of GLP-1 (7-36) amide from rat intestine," FEBS Letters, vol. 242 (1), Dec. 1988.
Lamy et al., Archives of Biochemistry and Biophysics, vol. 193, No. 1, pp. 140-149 (Mar. 1979).
M. Raida et al. "Liquid Chromatography and Electrospray Mass Spectrometric Mapping of Peptides from Human Plasma Filtrate" Journal of America Society of Mass Spectrometry. col. 10, pp. 45-54 (1999).
Johnson et al., Basic Liquid Chromatography, pp. 116-148 (1978).
Schmidt et al, "Glucagon-like peptide-1 but not glucagons-like peptide-2 stimulates insulin release from isolated rat pancreatic islets" Diabetologia, vol. 28. 28, pp. 704-707 (1985).

(Continued)

*Primary Examiner*—Christopher R. Tate
*Assistant Examiner*—Roy Teller
(74) *Attorney, Agent, or Firm*—Reza Green; Richard W. Bork

(57) ABSTRACT

Method for purifying a racemized polypeptide by ion-exchange chromatography.

56 Claims, 3 Drawing Sheets

OTHER PUBLICATIONS

Figure 1:
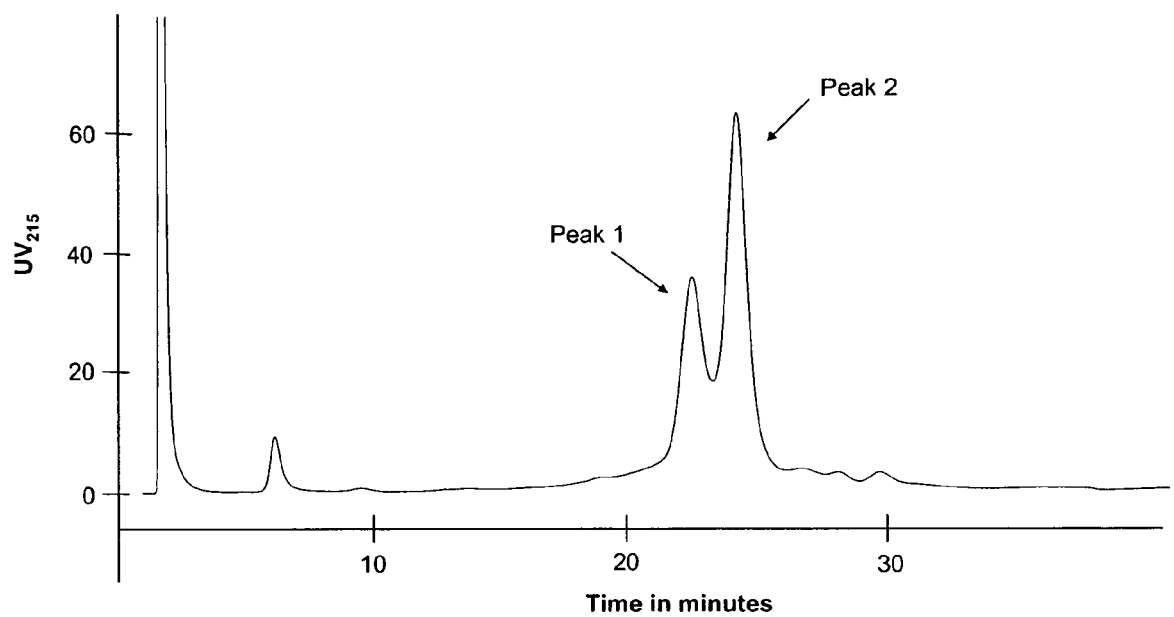

Stadalius et al., "Predicting Bandwidth In The High Performance Liquid Chromatographic Separation of Large Biomolecules II. A General Model For The Four Common High Performance Liquid Chromatography Methods" Journal of Chromatography, vol. 387, pp. 21-40 (1987).
Notice of Allowance in U.S. Appl. No. 09/671,461, sent from the USPTO on Oct. 2, 2006.
Non-final Office Action in U.S. Appl. No. 09/671,461, sent from the USPTO on Jan. 11, 2006.
Non-final Office Action in U.S. Appl. No. 09/671,461, sent from the USPTO on Jan. 9, 2006.
Non-final Office Action in U.S. Appl. No. 09/671,461, sent from the USPTO on May 31, 2005.
Final Office Action in U.S. Appl. No. 09/671,461, sent from the USPTO on Nov. 19, 2003.
Non-final Office Action in U.S. Appl. No. 09/671,461, sent from the USPTO on Feb. 11, 2003.
Non-final Office Action in U.S. Appl. No. 10/176,410, sent from the USPTO on Dec. 29, 2006.
Final Office Action in U.S. Appl. No. 10/176,410, sent from the USPTO on May 19, 2006.
Non-final Office Action in U.S. Appl. No. 10/176,410, sent from the USPTO on Jul. 14, 2005.
Non-final Office Action in U.S. Appl. No. 10/176,410, sent from the USPTO on Sep. 17, 2004.
Final Office Action in U.S. Appl. No. 11/807,558, sent from the USPTO on Nov. 20, 2009.
Non-final Office Action in U.S. Appl. No. 11/807,558, send from the USPTO on Apr. 13, 2009.

* cited by examiner

SEQUENCE LISTING

<160> NUMBER OF SEQ ID NOS: 8

<210> SEQ ID NO 1
<211> LENGTH: 29
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser

```
                 1               5                  10                 15
Arg Arg Ala Gln Asp Phe Val Gln Trp Leu Met Asn Thr
            20              25

<210> SEQ ID NO 2
<211> LENGTH: 31
<212> TYPE: PRT
<213> ORGANISM: Homo sapiens

<400> SEQUENCE: 2

His Ala Glu Gly Thr Phe Thr Ser Asp Val Ser Ser Tyr Leu Glu Gly
 1               5                  10                 15

Gln Ala Ala Lys Glu Phe Ile Ala Trp Leu Val Lys Gly Arg Gly
            20                  25                 30

<210> SEQ ID NO 3
<211> LENGTH: 33
<212> TYPE: PRT
<213> ORGANISM: Homo sapiens

<400> SEQUENCE: 3

His Ala Asp Gly Ser Phe Ser Asp Glu Met Asn Thr Ile Leu Asp Asn
 1               5                  10                 15

Leu Ala Ala Arg Asp Phe Ile Asn Trp Leu Ile Gln Thr Lys Ile Thr
            20                  25                 30

Asp

<210> SEQ ID NO 4
<211> LENGTH: 39
<212> TYPE: PRT
<213> ORGANISM: Glia monster
<220> FEATURE:
<221> NAME/KEY: MOD_RES
<222> LOCATION: (39)..(39)
<223> OTHER INFORMATION: Serine at position 39 is amidated

<400> SEQUENCE: 4

His Gly Glu Gly Thr Phe Thr Ser Asp Leu Ser Lys Gln Met Glu Glu
 1               5                  10                 15

Glu Ala Val Arg Leu Phe Ile Glu Trp Leu Lys Asn Gly Gly Pro Ser
            20                  25                 30

Ser Gly Ala Pro Pro Pro Ser
            35

<210> SEQ ID NO 5
<211> LENGTH: 39
<212> TYPE: PRT
<213> ORGANISM: Gila monster
<220> FEATURE:
<221> NAME/KEY: MOD_RES
<222> LOCATION: (39)..(39)
<223> OTHER INFORMATION: Serine at position 39 is amidated

<400> SEQUENCE: 5

His Ser Asp Gly Thr Phe Thr Ser Asp Leu Ser Lys Gln Met Glu Glu
 1               5                  10                 15

Glu Ala Val Arg Leu Phe Ile Glu Trp Leu Lys Asn Gly Gly Pro Ser
            20                  25                 30

Ser Gly Ala Pro Pro Pro Ser
            35

<210> SEQ ID NO 6
```

```
<211> LENGTH: 37
<212> TYPE: PRT
<213> ORGANISM: Homo sapiens

<400> SEQUENCE: 6

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asp Thr Lys Arg Asn
            20                  25                  30

Lys Asn Asn Ile Ala
        35

<210> SEQ ID NO 7
<211> LENGTH: 44
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (44)..(44)
<223> OTHER INFORMATION: Lysine at position 44 is amidated

<400> SEQUENCE: 7

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 8
<211> LENGTH: 33
<212> TYPE: PRT
<213> ORGANISM: Synthetic construct

<400> SEQUENCE: 8

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp
```

US 7,749,955 B2

SEPARATION OF POLYPEPTIDES COMPRISING A RACEMIZED AMINO ACID

FIELD OF THE INVENTION

The present invention relates to the field of protein purification. In particular, the invention relates to a method for separating polypeptides wherein an amino acid is racemized.

BACKGROUND OF THE INVENTION

Polypeptides are increasingly being used as medicaments for the treatment of diseases within all major therapy areas. Treatment of diabetes by chronic insulin administration has been practised for more than 80 years, and therapeutic applications of polypeptides within growth disorders and cancer also have been practised for many years.

Economical processes for the large scale production of polypeptides with a purity sufficiently high for therapeutic applications are crucial for further polypeptide-based therapies to reach the mass market and for the existing therapies to become more widely used.

Polypeptides for therapeutic applications are to be highly purified in order to be efficacious and in order to provide certainty for not causing adverse events upon administration to patients. A number of processing steps used in the synthesis and purification of polypeptides are known to cause racemization of one or more amino acid residues in the target polypeptide. Typically, these conditions are pH extremes and high temperatures, e.g. pH values at above pH 12 (Senderoff et al. J. Pharm. Sci. 87, 183-189 (1998)). The polypeptide variants having a racemized amino acid residue are amenable to separation and identification by state of the art analytical techniques. These variants are undesirable in polypeptides for therapeutic use due to toxicity concerns and because they may have different activity than the desired polypeptide. However, it is a serious challenge to separate these closely related polypeptides in preparative scale, i.e. during industrial manufacture.

Purification of a polypeptide from a mixture is a steps which is normally used several times during the overall manufacturing process for a therapeutic polypeptide. Ion exchange chromatography is often applied in the early and crude separation steps, whereas reverse phase high pressure liquid chromatography (RP-HPLC) is the preferred method for industrial high resolution separation of related polypeptides in the final purification steps. RP-HPLC has proven versatile for the large scale purification of many polypeptides but the process is relatively expensive and has limited capacity.

We have surprisingly found an ion exchange process which can separate the two polypeptide variant the result when racemization of an amino acid residue has taken place. The method is amenable for large scale operation and provides an economical purification step with high capacity.

BREIF DECRPTION OF THE DRAWINGS

FIG. 1. Chromatogram of $AU_{280}$ versus time (min) from a separation. Peak no. 1 is the D-his variant, D-His$^7$Arg$^{34}$Lys$^{26}$N$^\epsilon$($\gamma$-Glu(N$^\alpha$-hexadecanoyl))GLP-1$_{(7-37)}$, peak no. 2 is Arg$^{34}$Lys$^{26}$N$^\epsilon$($\gamma$-Glu(N$^\alpha$-hexadecanoyl))GLP-1$_{(7-37)}$.

Figure 2:
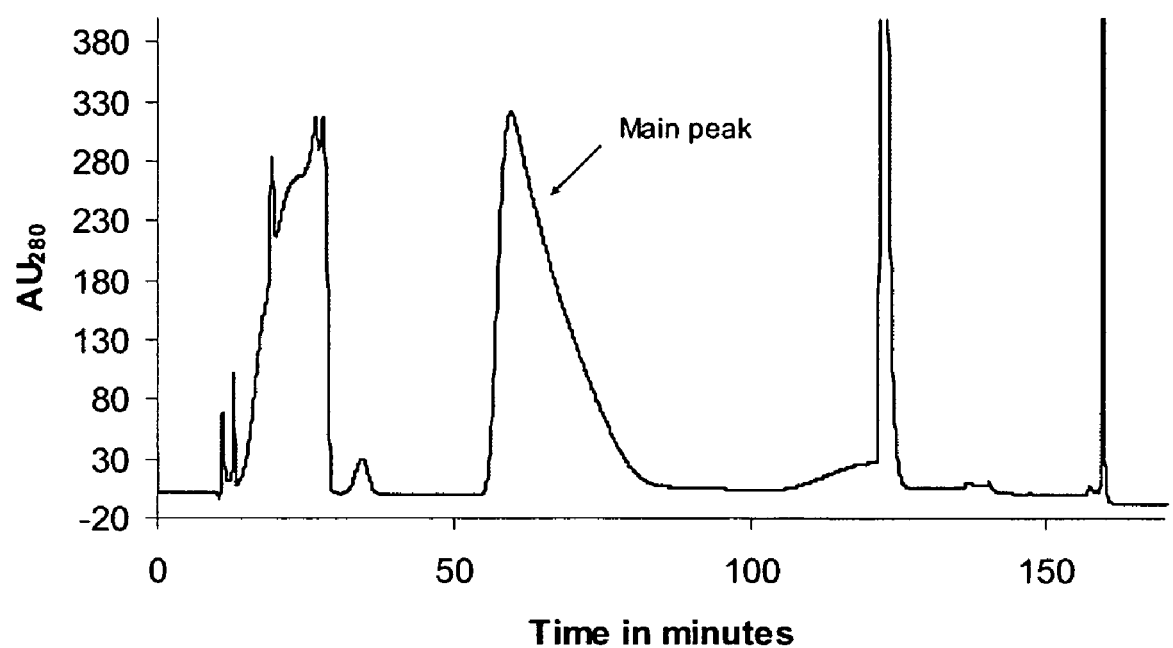

FIG. 2. Chromatogram of $AU_{280}$ versus time (min) from a separation. Both D-His$^7$Arg$^{34}$Lys$^{26}$N$^\epsilon$($\gamma$-Glu(N$^\alpha$-hexadecanoyl))GLP-1$_{(7-37)}$ and Arg$^{34}$Lys$^{26}$N$^\epsilon$($\gamma$-Glu(N$^\alpha$-hexadecanoyl))GLP-1$_{(7-37)}$ elutes in the main peak. The D-His variant is highly concentrated in the leading edge of the main peak and can be separated with low loss of yield by fractionation or peak cutting.

Figure 3:
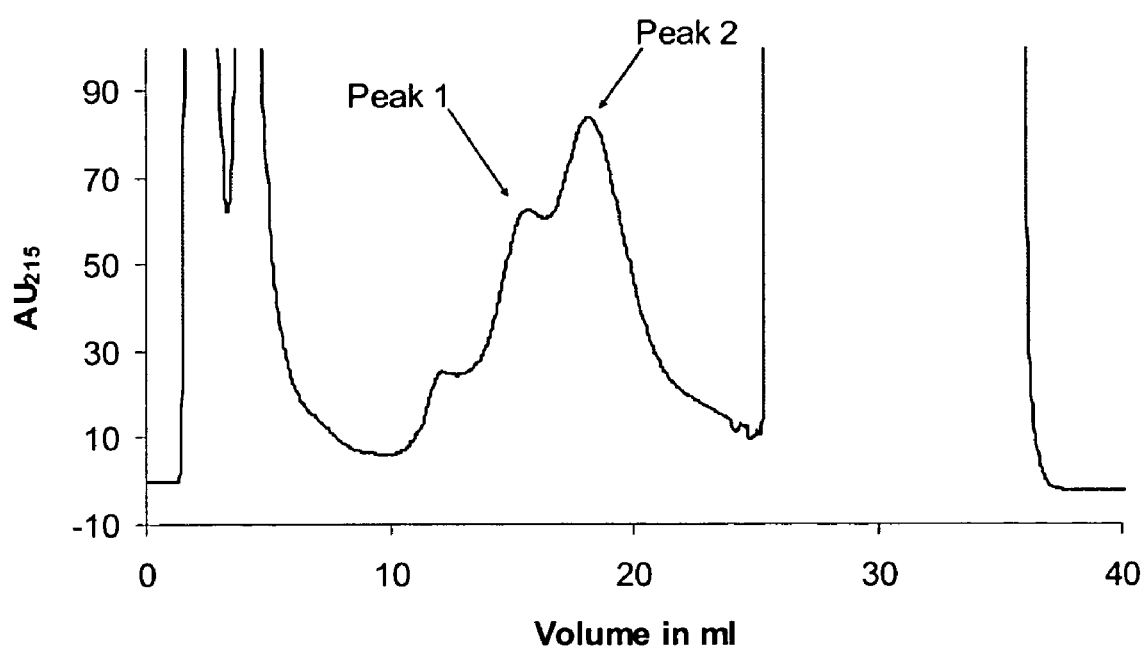

FIG. 3. Chromatogram of $AU_{215}$ versus volume (mL) from a separation. Peak no. 1 contains the L-His variant of Exendin-4, peak no. 2 contains the D-His variant of Exendin-4.

DEFINITIONS

The following is a detailed definition of the terms used in the specification.

The term "buffer" as used herein refers to a chemical compound that reduces the tendency of pH of a solution such as chromatographic solutions to change over time as would otherwise occur. Buffers include the following non-limiting examples: sodium acetate, sodium carbonate, sodium citrate, glycylglycine, glycine, histidine, lysine, sodium phosphate, borate, Tris-hydroxymethyl-aminomethane, ethanolamine and mixtures thereof.

The term "organic modifier" as used herein refers to an organic compound which is added to chromatographic solutions. Organic modifiers may be monohydric alcohols, polyhydric alcohols as well as nitriles and ketones. Non-limiting examples of organic modifiers are methanol, ethanol, 1-propanol, 2-propanol, t-butanol, hexylene glycol (4-methyl-2,4-pentanediol), neopentyl alcohol (2,2-dimethyl-1,3-propanediol), acetonitrile, acetone and urea.

The term "polypeptide" as used herein means a compound composed of at least five constituent amino acids connected by peptide bonds. The constituent amino acids may be from the group of the amino acids encoded by the genetic code and they may natural amino acids which are not encoded by the genetic code, as well as synthetic amino acids. Natural amino acids which are not encoded by the genetic code are e.g. hydroxyproline, $\gamma$-carboxyglutamate, ornithine, phosphoserine, D-alanine and D-glutamine. Synthetic amino acids comprise amino acids manufactured by chemical synthesis, i.e. D-isomers of the amino acids encoded by the genetic code such as D-alanine and D-leucine, Aib ($\alpha$-aminoisobutyric acid), Abu ($\alpha$-aminobutyric acid), Tle (tert-butylglycine), and $\beta$-alanine. A polypeptide may comprise a single peptide chain or it may comprise more than one peptide chain, such as e.g. human insulin where two chains are connected by disulphide bonds.

The term "glucagon-like peptide" as used herein refers to the exendins and the homologous peptides besides glucagon which are derived from the preproglucagon gene, i.e. glucagon-like peptide 1 (GLP-1), glucagon-like peptide 2 (GLP-2), and oxynthomodulin (OXM) as well as analogues and derivatives thereof. The peptides derived from the preproglucagon gene are glucagon, glucagon-like peptide 1 (GLP-1), glucagon-like peptide 2 (GLP-2) and oxyntomodulin (OXM). The exendins which are found in the Gila monster are homologous to GLP-1 and also exert an insulinotropic effect. Examples of exendins are exendin-4 and exendin-3.

The glucagon-like peptides have the following sequences (SEQ ID Nos. 1-6):

```
             1    5    10   15   20   25   30   35
Glucagon  HSQGT FTSDY SKYLD SRRAQ DFVQW LMNT
```

```
                -continued
GLP-1      HAEGT FTSDV SSYLE GQAAK EFIAW LVKGR G

GLP-2      HADGS FSDEM NTILD NLAAR DFINW LIQTK ITD

Exendin-4  HGEGT FTSDL SKQME EEAVR LFIEW LKNGG PSSGA PPPS-NH2

Exendin-3  HSDGT FTSDL SKQME EEAVR LFIEW LKNGG PSSGA PPPS-NH2

OXM        HSQGT FTSDY SKYLD SRRAQ DFVQW LMDTK RNKNN IA
```

The term "analogue" as used herein referring to a peptide means a modified peptide wherein one or more amino acid residues of the peptide have been substituted by other amino acid residues and/or wherein one or more amino acid residues have been deleted from the peptide and/or wherein one or more amino acid residues have been deleted from the peptide and or wherein one or more amino acid residues have been added to the peptide. Such addition or deletion of amino acid residues can take place at the N-terminal of the peptide and/or at the C-terminal of the peptide. Two different and simple systems are often used to describe analogues: For example $Arg^{34}$-GLP-1(7-37) or K34R-GLP-1(7-37) designates a GLP-1 analogue wherein the naturally occuring lysine at position 34 has been substituted with arginine (standard single letter abbreviation for amino acids used according to IUPAC-IUB nomenclature).

The term "derivative" as used herein in relation to a parent peptide means a chemically modified parent protein or an analogue thereof, wherein at least one substituent is not present in the parent protein or an analogue thereof, i.e. a parent protein which has been covalently modified. Typical modifications are amides, carbohydrates, alkyl groups, acyl groups, esters, pegylations and the like. An examples of a derivative of GLP-1(7-37) is $Arg^{34}$, $Lys^{26}(N^{\epsilon}$-($\gamma$-Glu($N^{\alpha}$-hexadecanoyl)))-GLP-1(7-37).

The term "a fragment thereof" as used herein in relation to a peptide means any fragment of the peptide having at least 20% of the amino acids of the parent peptide. Thus, for human serum albumin a fragment would comprise at least 117 amino acids as human serum albumin has 585 amino acids. In one embodiment the fragment has at least 35% of the amino acids of the parent peptide. In another embodiment the fragment has at least 50% of the amino acids of the parent peptide. In another embodiment the fragment has at least 75% of the amino acids of the parent peptide.

The term "variant" as used herein in relation to a peptide means a modified peptide which is an analog of the parent peptide, a derivative of the parent peptide or a derivative of an analog of the parent peptide.

The term "GLP-1 peptide" as used herein means GLP-1(7-37), an analogue of GLP-1(7-37), a derivative of GLP-1(7-37) or a derivative of a GLP-1(7-37) analogue.

The term "GLP-2 peptide" as used herein means GLP-2(1-33), an analogue of GLP-2, a derivative of GLP-2(1-33) or a derivative of a GLP-2(1-33) analogue.

The term "exendin-4 peptide" as used herein means exendin-4(1-39), an exendin-4 analogue, an exendin-4 derivative or a derivative of an exendin-4 analogue.

The term "stable exendin-4 compound" as used herein means a chemically modified exendin-4(1-39), i.e. an analogue or a derivative which exhibits an in vivo plasma elimination half-life of at least 10 hours in man, as determined by the following method. The method for determination of plasma elimination half-life of an exendin-4 compound in man is: The compound is dissolved in an isotonic buffer, pH 7.4, PBS or any other suitable buffer. The dose is injected peripherally, preferably in the abdominal or upper thigh. Blood samples for determination of active compound are taken at frequent intervals, and for a sufficient duration to cover the terminal elimination part (e.g. Pre-dose, 1, 2, 3, 4, 5, 6, 7, 8, 10, 12, 24 (day 2), 36 (day 2), 48 (day 3), 60 (day 3), 72 (day 4) and 84 (day 4) hours post dose). Determination of the concentration of active compound is performed as described in Wilken et al., Diabetologia 43(51):A143, 2000. Derived pharmacokinetic parameteres are calculated from the concentration-time data for each individual subject by use of non-compartmental methods, using the commercially available software WinNonlin Version 2.1 (Pharsight, Cary, N.C., USA). The terminal elimination rate constant is estimated by log-linear regression on the terminal log-linear part of the concentration-time curve, and used for calculating the elimination half-life.

The term "DPP-IV protected glucagon-like peptide" as used herein means a glucagon-like peptide which is chemically modified as compared to the natural peptide to render said glucagon-like peptide more resistant to the plasma peptidase dipeptidyl aminopeptidase-4 (DPP-IV).

The term "immunomodulated exendin-4 compound" as used herein means an exendin-4 peptide which is an analogue or a derivative of exendin-4(1-39) having a reduced immune response in humans as compared to exendin-4(1-39). The method for assessing the immune response is to measure the concentration of antibodies reactive to the exendin-4 compound after 4 weeks of treatment of the patient.

The term "insulin peptide" as used herein means a peptide which is either human insulin or a chemically modified human insulin, such as an analog or a derivative thereof.

The term "human insulin" as used herein means the human hormone whose structure and properties are well known. Human insulin has two polypeptide chains that are connected by disulphide bridges between cysteine residues, namely the A-chain and the B-chain. The A-chain is a 21 amino acid peptide and the B-chain is a 30 amino acid peptide, the two chains being connected by three disulphide bridges: one between the cysteines in position 6 and 11 of the A-chain, the second between the cysteine in position 7 of the A-chain and the cysteine in position 7 of the B-chain, and the third between the cysteine in position 20 of the A-chain and the cysteine in position 19 of the B-chain.

The term "polypeptide product" as used herein means the purified peptide product which is to be used for the manufacture of a pharmaceutical composition. Thus, the polypeptide product is normally obtained as the product from the final purification, drying or conditioning step. The product may be crystals, precipitate, solution or suspension. The polypeptide product is also known in the art as the drug substance, i.e. the active pharmaceutical ingredient.

The term "isoelectric point" as used herein means the pH value where the overall net charge of a macromolecule such as a polypeptide is zero. In polypeptides there may be many charged groups, and at the isoelectric point the sum of all these charges is zero. At a pH above the isoelectric point the overall net charge of the polypeptide will be negative, whereas at pH values below the isoelectric point the overall net charge of the polypeptide will be positive.

The term "pharmaceutically acceptable" as used herein means suited for normal pharmaceutical applications, i.e. giving rise to no adverse events in patients etc.

The term "excipient" as used herein means the chemical compounds which are normally added to pharmaceutical compositions, e.g. buffers, tonicity agents, preservatives and the like.

The term "effective amount" as used herein means a dosage which is sufficient to be effective for the treatment of the patient compared with no treatment.

The term "pharmaceutical composition" as used herein means a product comprising an active compound or a salt thereof together with pharmaceutical excipients such as buffer, preservative, and optionally a tonicity modifier and/or a stabilizer. Thus a pharmaceutical composition is also known in the art as a pharmaceutical formulation.

The term "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

DESCRIPTION OF THE INVENTION

In a first aspect the present invention relates to a method for separating the two forms of a polypeptide having a single amino acid racemization, characterized in being an ion exchange chromatography process comprising elution by increasing the salt concentration at a pH that is no more than about 2 pH units from a pKa of the racemized amino acid residue under the conditions of elution.

In another aspect the present invention relates to a method for separating the two forms of a polypeptide having a single amino acid racemization, characterized in being an ion exchange chromatography process comprising elution by increasing the salt concentration at a pH that is no more than about 1 pH unit from a pKa of the racemized amino acid residue under the conditions of elution.

In another aspect the present invention relates to a method for separating the two forms of a polypeptide having a single amino acid racemization, characterized in being an ion exchange chromatography process comprising elution by increasing the salt concentration at a pH that is no more than 1 pH unit from a pKa of the racemized amino acid residue under the conditions of elution.

In another aspect the present invention relates to a method for separating the two polypeptides A(X) and A(X*), wherein
X is an L-amino acid,
A(X) is a polypeptide comprising the amino acid X,
X* is the D-isomer of X,
A(X*) is a polypeptide comprising the amino acid X* but otherwise identical to A(X), said method characterized in being an ion exchange chromatography process comprising elution by increasing the salt concentration at a pH that is no more than 2 pH unit from a pKa of X under the conditions of elution.

In another aspect of the present invention relates to a method for separating two polypeptides having a single amino acid racemization, A(X) and A(X*), wherein
X is an L-amino acid,
A(X) is a polypeptide comprising the amino acid X,
X* is the D-isomer of X,
A(X*) is a polypeptide comprising the amino acid X* but otherwise identical to A(X), said method characterized in being an ion exchange chromatography process comprising elution by increasing the salt concentration at a pH that is no more than about 1 pH unit from a pKa of X under the conditions of elution.

The target polypeptide and the impurity comprising a racemized amino acid residue are eluted and separated by an isocratic, step, asymptotic or linear increase in the salt concentration of the eluent, or in combinations of these. The pKa of X may be assessed by tabulated pKa values for amino acid residues (see e.g. Creighton T. E. "Proteins. Structures and Molecular Properties", page 6, $2^{nd}$ ed. W.H. Freeman and Company, N.Y. (1993)). The pKa of X may also be assessed by computer-implemented algorithms known in the art which take into account the effects of neightboring amino acid residues on the pKa of X. Another possibility to determine the pKa of X is to perform NMR studies of the protein wherein X is incorporated. It is known that pKa values may be influenced by the composition of the solution, e.g. the presence of an organic modifier may change the pKa of an amino acid residue.

Ion exchange chromatography is a widely applied separation process wherein the separation is achieved on the basis of charges carried by solute molecules. In ion exchange chromatography the major separation principle is ionic interactions between the stationary phase and the soluble molecules being separated.

In the normal mode of ion exchange chromatography a complete cyclus comprises
  a) equilibration with an equilibration buffer to bring the column in a state where it is ready for a cyclus,
  b) application of the product holding sample,
  c) an optional washing step where the chromatographic stationary phase with the bound product is washed,
  d) elution where increased salt concentration causes the affinity of the product towards the chromatography stationary phase to decrease and the product leaves the column in the chromatographic column eluate, and
  e) an optional regeneration where it is attempted to strip the chromatographic stationary phase from remaining impurities using a regeneration solution.

During the elution step (d) the separation of different polypeptides is obtained by collecting the column eluate into a number of pools. By proper collection of these pools, e.g. by measurement of the $AU_{280}$ (i.e. absorbance at 280 nm) or the conductivity, each of these pools predominantly contain certain polypeptides. Thus, separation is achieved by collecting those pools or the part of the eluent predominantly containing the desired polypeptide.

The equilibration solution and the sample for application may or may not contain the organic modifier. The organic modifier could be but is not limited to any monohydric aliphatic alcohol (methanol, ethanol, propanois and butanols) or a polyhydric alcohol such as hexylene glycol or neopentyl alcohol. Salt components for any section of the chromatographic purification may be any salt including but not limited to: NaCl, KCl, $NH_4Cl$, $CaCl_2$, sodium acetate, potassium acetate, ammonium acetate etc. Any buffer component can be used including but not limited to: citric buffers, phosphate buffers, borate buffers, carbonate buffers, acetate buffers, ammonium buffers, glycin buffers, tris-hydroxymethyl amino-methane buffers, 4-(2-hydroxyethyl)piperazine-1-ethanesulfonic acid buffers etc. A wide range of chromatographic ion exchange resins are applicable, including but not limited to Mono Q (Amersham Biosciences), Source 15Q or 30Q (Amersham Biosciences), Poros 20HQ or 50HQ (Perspective Biosystems), Toyopearl Q650S (Toso Haas) and others.

In one embodiment of the present invention the method is for separating said polypeptides in preparative scale.

In another embodiment of the present invention elution is performed at a pH which is substantially the same as the pH used for binding. However, it is also possible perform the binding, i.e. application of the sample, to the column at a pH which is not the same as the pH used for elution. Binding at a pH which is different from the pH used for elution thus implies that a pH adjustment is performed on the column.

In another embodiment of the present invention elution of the polypeptides is performed at a pH which is no more than about 0.75 pH units from a pKa of X under the conditions of elution. In another embodiment of the present invention elution of the polypeptides is performed at a pH which is no more than about 1.0 pH units from a pKa of X under the conditions of elution. In another embodiment of the present invention elution of the polypeptides is performed at a pH which is no more than about 0.5 pH units from a pKa of X under the conditions of elution. In another embodiment of the present invention elution of the polypeptides is performed at a pH which is no more than about 0.25 pH units from a pKa of X under the conditions of elution.

In one embodiment of the present invention elution is performed at a pH which is higher than the isoelectric point of said polypeptides. In another embodiment of the present invention elution is performed at a pH which is lower than the isoelectric point of said polypeptides In another embodiment of the present invention polypeptide has a molecular weight of less than about 10 kDa.

In another embodiment of the present invention polypeptide has a molecular weight of less than about 8 kDa.

In another embodiment of the present invention polypeptide has a molecular weight in the range from about 1 kDa to about 10 kDa.

In another embodiment of the present invention the eluent comprises an organic modifier.

In another embodiment of the present invention the eluent comprises an organic modifier in a concentration sufficient to keep said polypeptides soluble.

In another embodiment of the present invention the organic modifier is ethanol.

In another embodiment of the present invention the organic modifier is 2-propanol.

In another embodiment of the present invention the organic modifier is acetonitril.

In another embodiment of the present invention the organic modifier is selected from the group consisting of methanol, 1-propanol and hexylene glycol.

In another embodiment of the present invention the organic modifier is neopentyl alcohol.

In another embodiment of the present invention the concentration of the organic modifier is from about 10% to about 80%, such as from about 20% to about 70%, or from about 30% to about 65%.

In another embodiment of the present invention the salt is selected from the group consisting of sodium chloride, sodium sulphate, sodium acetate, potassium chloride, potassium sulphate, and potassium acetate.

In another embodiment of the present invention X is the N-terminal or the C-terminal amino acid residue.

In another embodiment of the present invention X is L-histidine.

In another embodiment of the present invention X is an amino acid analogue of histidine.

In another embodiment of the present invention X is selected from the group consisting of desamino-histidine, 2-amino-histidine, β-hydroxy-histidine, homohistidine, α-fluoromethyl-histidine and α-methyl-histidine.

In another embodiment of the present invention X is the N-terminal amino acid residue.

In another embodiment of the present invention X is L-phenylalanine.

In another embodiment of the present invention X is L-lysine.

In another embodiment of the present invention X is L-arginine.

In another embodiment of the present invention X is L-aspartic acid.

In another embodiment of the present invention X is L-aspargine

In another embodiment of the present invention X is L-glutamic acid.

In another embodiment of the present invention X is L-glutamine.

In another embodiment of the present invention X is L-γ-carboxyglutamic acid.

In another embodiment of the present invention the polypeptide is a glucagon-like peptide.

In another embodiment of the present invention the polypeptide is glucagon, a glucagon analogue, a derivative of glucagon or a derivative of a glucagon analogue.

In another embodiment of the present invention the glucagon-like peptide is GLP-1, a GLP-1 analogue, a derivative of GLP-1 or a derivative of a GLP-1 analogue.

In another embodiment of the present invention the GLP-1 analogue is selected from the group consisting of $Arg^{34}$-GLP-1 (7-37), $Gly^8$-GLP-1 (7-36)-amide, $Gly^8$-GLP-1 (7-37), $Val^8$-GLP-1 (7-36)-amide, $Val^8$-GLP-1(7-37), $Val^8Asp^{22}$-GLP-1(7-36)-amide, $Val^8Asp^{22}$-GLP-1(7-37), $Val^8Glu^{22}$-GLP-1(7-36)-amide, $Val^8Glu^{22}$-GLP-1(7-37), $Val^8Lys^{22}$-GLP-1(7-36)-amide, $Val^8Lys^{22}$-GLP-1(7-37), $Val^8Arg^{22}$-GLP-1(7-36)-amide, $Val^8Arg^{22}$-GLP-1(7-37), $Val^8His^{22}$-GLP-1(7-36)-amide, $Val^8His^{22}$-GLP-1(7-37), $Val^8Trp^{19}Glu^{22}$-GLP-1(7-37), $Val^8Glu^{22}Val^{25}$-GLP-1(7-37), $Val^8Tyr^{16}Glu^{22}$-GLP-1(7-37), $Val^8Trp^{16}Glu^{22}$-GLP-1(7-37), $Val^8Leu^{16}Glu^{22}$-GLP-1(7-37), $Val^8Tyr^{18}Glu^{22}$-GLP-1(7-37), $Val^8Glu^{22}His^{37}$-GLP-1(7-37), $Val^8Glu^{22}Ile^{33}$-GLP-1(7-37), $Val^8Trp^{16}Glu^{22}Val^{25}Ile^{33}$-GLP-1(7-37), $Val^8Trp^{16}Glu^{22}Ile^{33}$-GLP-1(7-37), $Val^8Glu^{22}Val^{25}Ile^{33}$-GLP-1(7-37), $Val^8Trp^{16}Glu^{22}Val^{25}$-GLP-1(7-37), analogues thereof and derivatives of any of these.

In another embodiment of the present invention the derivative of GLP-1 or a derivative of a GLP-1 analogue has a lysine residue, such as one lysine, wherein a lipophilic substituent optionally via a spacer is attached to the epsilon amino group of said lysine.

In another embodiment of the present invention the lipophilic substituent has from 8 to 40 carbon atoms, preferably from 8 to 24 carbon atoms, e.g. 12 to 18 carbon atoms.

In another embodiment of the present invention the spacer is present and is selected from an amino acid, e.g. beta-Ala, L-Glu, or aminobutyroyl.

In another embodiment of the present invention the glucagon-like peptide is a DPPIV-protected glucagon-like peptide.

In another embodiment of the present invention the glucagon-like peptide is a plasma stable glucagon-like peptide.

In another embodiment of the present invention the glucagon-like peptide is a derivative of a GLP-1 analogue which is $Arg^{34} Lys^{26}(N^\epsilon\text{-}(\gamma\text{-}Glu(N^\alpha\text{-hexadecanoyl})))$-GLP-1(7-37).

In another embodiment of the present invention the glucagon-like peptide is a GLP-1 peptide which has from 22 to 40 amino acid residues, preferable from 26 to 36 amino acid residues, even more preferable from 29 to 33 amino acid residues.

In one embodiment of the present invention the glucagon-like peptide is GLP-2, a GLP-2 analogue, a derivative of GLP-2 or a derivative of a GLP-2 analogue.

In another embodiment of the present invention the derivative of GLP-2 or a derivative of a GLP-2 analogue has a lysine residue, such as one lysine, wherein a lipophilic substituent optionally via a spacer is attached to the epsilon amino group of said lysine.

In another embodiment of the present invention the lipophilic substituent has from 8 to 40 carbon atoms, preferably from 8 to 24 carbon atoms, e.g. 12 to 18 carbon atoms.

In another embodiment of the present invention the spacer is present and is selected from an amino acid, e.g. beta-Ala, L-Glu, aminobutyroyl.

In another embodiment of the present invention the glucagon-like peptide has from 27 to 39 amino acid residues, preferable from 29 to 37 amino acid residues, even more preferable from 31 to 35 amino acid residues.

In another embodiment of the invention the glucagon-like peptide is $Lys^{17}Arg^{30}$-GLP-2(1-33) or $Arg^{30}Lys^{17}N^{\epsilon}(\beta$-Ala $(N^{\alpha}$-hexadecanoyl)) GLP-2(1-33).

In another embodiment of the present invention the glucagon-like peptide is $Gly^2$-GLP-2(1-33).

In one embodiment of the present invention the glucagon-like peptide is exendin-4, an exendin-4 analogue, a derivative of exendin-4, or a derivative of an exendin-4 analogue.

In another embodiment of the present invention the glucagon-like peptide is exendin-4.

In another embodiment of the present invention the derivative of exendin-4 or derivative of an exendin-4 analogue is an acylated peptide or a pegylated peptide.

In another embodiment of the present invention the glucagon-like peptide is a stable exendin-4 compound.

In another embodiment of the present invention the glucagon-like peptide is a DPP-IV protected exendin-4 compound.

In another embodiment of the present invention the glucagon-like peptide is an immunomodulated exendin-4 compound.

In another embodiment of the present invention the derivative of exendin-4 or derivative of an exendin-4 analogue has a lysine residue, such as one lysine, wherein a lipophilic substituent optionally via a spacer is attached to the epsilon amino group of said lysine.

In another embodiment of the present invention the lipophilic substituent has from 8 to 40 carbon atoms, preferably from 8 to 24 carbon atoms, e.g. 12 to 18 carbon atoms.

In another embodiment of the present invention the spacer is present and is selected from an amino acid, e.g. beta-Ala, L-Glu, or aminobutyroyl.

In another embodiment of the present invention the glucagon-like peptide is an exendin-4 peptide which has from 30 to 48 amino acid residues, from 33 to 45 amino acid residues, preferable from 35 to 43 amino acid residues, even more preferable from 37 to 41 amino acid residues.

In one embodiment of the invention the GLP-2 peptide is selected from the list consisting of: K30R-GLP-2(1-33); S5K-GLP-2(1-33); S7K-GLP-2(1-33); D8K-GLP-2(1-33); E9K-GLP-2(1-33); M10K-GLP-2(1-33); N11K-GLP-2(1-33); T12K-GLP-2(1-33); I13K-GLP-2(1-33); L14K-GLP-2(1-33); D15K-GLP-2(1-33); N16K-GLP-2(1-33); L17K-GLP-2(1-33); A18K-GLP-2(1-33); D21K-GLP-2(1-33); N24K-GLP-2(1-33); Q28K-GLP-2(1-33); S5K/K30R-GLP-2(1-33); S7K/K30R-GLP-2(1-33); D8K/K30R-GLP-2(1-33); E9K/K30R-GLP-2(1-33); M10K/K30R-GLP-2(1-33); N11K/K30R-GLP-2(1-33); T12K/K30R-GLP-2(1-33); I13K/K30R-GLP-2(1-33); L14K/K30R-GLP-2(1-33); D15K/K30R-GLP-2(1-33); N16K/K30R-GLP-2(1-33); L17K/K30R-GLP-2(1-33); A18K/K30R-GLP-2(1-33); D21K/K30R-GLP-2(1-33); N24K/K30R-GLP-2(1-33); Q28K/K30R-GLP-2(1-33); K30R/D33K-GLP-2(1-33); D3E/K30R/D33E-GLP-2(1-33); D3E/S5K/K30R/D33E-GLP-2(1-33); D3E/S7K/K30R/D33E-GLP-2(1-33); D3E/D8K/K30R/D33E-GLP-2(1-33); D3E/E9K/K30R/D33E-GLP-2(1-33); D3E/M10K/K30R/D33E-GLP-2(1-33); D3E/N11K/K30R/D33E-GLP-2(1-33); D3E/T12K/K30R/D33E-GLP-2(1-33); D3E/I13K/K30R/D33E-GLP-2(1-33); D3E/L14K/K30R/D33E-GLP-2(1-33); D3E/D15K/K30R/D33E-GLP-2(1-33); D3E/N16K/K30R/D33E-GLP-2(1-33); D3E/L17K/K30R/D33E-GLP-2(1-33); D3E/A18K/K30R/D33E-GLP-2(1-33); D3E/D21K/K30R/D33E-GLP-2(1-33); D3E/N24K/K30R/D33E-GLP-2(1-33); D3E/Q28K/K30R/D33E-GLP-2(1-33); and derivatives thereof.

In one embodiment of the invention the GLP-2 derivative is selected from the group consisting of S5K(3-(hexadecanoylamino)propionyl)-GLP-2(1-33); S7K(3-(hexadecanoylamino)propionyl)-GLP-2(1-33); D8K(3-(hexadecanoylamino)propionyl)-GLP-2(1-33); E9K(3-(hexadecanoylamino)propionyl)-GLP-2(1-33); M10K(3-(hexadecanoylamino)propionyl)-GLP-2(1-33); N11K(3-(hexadecanoylamino)propionyl)-GLP-2(1-33); T12K(3-(hexadecanoylamino)propionyl)-GLP-2(1-33); I13K(3-(hexadecanoylamino)propionyl)-GLP-2(1-33); L14K(3-(hexadecanoylamino)propionyl)-GLP-2(1-33); D15K(3-(hexadecanoylamino)propionyl)-GLP-2(1-33); N16K(3-(hexadecanoylamino)propionyl)-GLP-2(1-33); L17K(3-(octanoylamino)propionyl)-GLP-2(1-33); L17K(3-(nonanoylamino)propionyl)-GLP-2(1-33); L17K(3-(decanoylamino)propionyl)-GLP-2(1-33); L17K(3-(undecanoylamino)propionyl)-GLP-2(1-33); L17K(3-(dodecanoylamino)propionyl)-GLP-2(1-33); L17K(3-(tridecanoylamino)propionyl)-GLP-2(1-33); L17K(3-(tetradecanoylamino)propionyl)-GLP-2(1-33); L17K(3-(pentadecanoylamino)propionyl)-GLP-2(1-33); L17K(3-(hexadecanoylamino)propionyl)-GLP-2(1-33); L17K(3-(heptadecanoylamino)propionyl)-GLP-2(1-33); L17K(3-(octadecanoylamino)propionyl)-GLP-2(1-33); L17K(3-(nonadecanoylamino)propionyl)-GLP-2(1-33); L17K(3-(eicosanoylamino)propionyl)-GLP-2(1-33); L17K((S)-4-carboxy-4-(octanoylamino)butanoyl)-GLP-2(1-33); L17K((S)-4-carboxy-4-(nonanoylamino)butanoyl)-GLP-2(1-33); L17K((S)-4-carboxy-4-(decanoylamino)butanoyl)-GLP-2(1-33); L17K((S)-4-carboxy-4-(undecanoylamino)butanoyl)-GLP-2(1-33); L17K((S)-4-carboxy-4-(dodecanoylamino)butanoyl)-GLP-2(1-33); L17K((S)-4-carboxy-4-(tridecanoylamino)butanoyl)-GLP-2(1-33); L17K((S)-4-carboxy-4-(tetradecanoylamino)butanoyl)-GLP-2(1-33); L17K((S)-4-carboxy-4-(pentadecanoylamino)butanoyl)-GLP-2(1-33); L17K((S)-4-carboxy-4-(hexadecanoylamino)butanoyl)-GLP-2(1-33); L17K((S)-4-carboxy-4-(heptadecanoylamino)butanoyl)-GLP-2(1-33); L17K((S)-4-carboxy-4-(octadecanoylamino)butanoyl)-GLP-2(1-33); L17K((S)-4-carboxy-4-(nonadecanoylamino)butanoyl)-GLP-2(1-33); L17K((S)-4-carboxy-4-(eicosanoylamino)butanoyl)-GLP-2(1-33); L17K(4-(octanoylamino)butanoyl)-GLP-2(1-33); L17K(4-(nonanoylamino)butanoyl)-GLP-2(1-33); L17K(4-(decanoylamino)butanoyl)-GLP-2(1-33); L17K(4-(undecanoylamino)butanoyl)-GLP-2(1-33); L17K(4-(dodecanoylamino)butanoyl)-GLP-2(1-33); L17K(4-(tridecanoylamino)butanoyl)-GLP-2(1-33); L17K(4-(tetradecanoylamino)butanoyl)-GLP-2(1-33); L17K(4-(pentadecanoylamino)butanoyl)-GLP-2(1-33); L17K(4-

(hexadecanoylamino)butanoyl)-GLP-2(1-33); L17K(4-(heptadecanoylamino)butanoyl)-GLP-2(1-33); L17K(4-(octadecanoylamino)butanoyl)-GLP-2(1-33); L17K(4-(nonadecanoylamino)butanoyl)-GLP-2(1-33); L17K(4-(eicosanoylamino)butanoyl)-GLP-2(1-33); A18K(3-(hexadecanoylamino)propionyl)-GLP-2(1-33); D21 K(3-(hexadecanoylamino)propionyl)-GLP-2(1-33); N24K(3-(hexadecanoylamino)propionyl)-GLP-2(1-33); Q28K(3-(hexadecanoylamino)propionyl)-GLP-2(1-33); S5K(3-(hexadecanoylamino)propionyl)/K30R-GLP-2(1-33); S7K(3-(hexadecanoylamino)propionyl)/K30R-GLP-2(1-33); D8K(3-(hexadecanoylamino)propionyl)/K30R-GLP-2(11-33); E9K(3-(hexadecanoylamino)propionyl)/K30R-GLP-2(1-33); M10K(3-(hexadecanoylamino)propionyl)/K30R-GLP-2(1-33); N11K(3-(hexadecanoylamino)propionyl)/K30R-GLP-2(1-33); T12K(3-(hexadecanoylamino)propionyl)/K30R-GLP-2(1-33); I13K(3-(hexadecanoylamino)propionyl)/K30R-GLP-2(1-33); L14K(3-(hexadecanoylamino)propionyl)/K30R-GLP-2(1-33); D15K(3-(hexadecanoylamino)propionyl)/K30R-GLP-2(1-33); N16K(3-(hexadecanoylamino)propionyl)/K30R-GLP-2(1-33); L17K(3-(octanoylamino)propionyl)/K30R-GLP-2(1-33); L17K(3-(nonanoylamino)propionyl)/K30R-GLP-2(1-33); L17K(3-(decanoylamino)propionyl)/K30R-GLP-2(1-33); L17K(3-(undecanoylamino)propionyl)/K30R-GLP-2(1-33); L17K(3-(dodecanoylamino)propionyl)/K30R-GLP-2(1-33); L17K(3-(tridecanoylamino)propionyl)/K30R-GLP-2(1-33); L17K(3-(tetradecanoylamino)propionyl)/K30R-GLP-2(1-33); L17K(3-(pentadecanoylamino)propionyl)/K30R-GLP-2(1-33); L17K(3-(hexadecanoylamino)propionyl)/K30R-GLP-2(1-33); L17K(3-(heptadecanoylamino)propionyl)/K30R-GLP-2(1-33); L17K(3-(octadecanoylamino)propionyl)/K30R-GLP-2(1-33); L17K(3-(nonadecanoylamino)propionyl)/K30R-GLP-2(1-33); L17K(3-(eicosanoylamino)propionyl)/K30R-GLP-2(1-33); L17K((S)-4-carboxy-4-(octanoylamino)butanoyl)/K30R-GLP-2(1-33); L17K((S)-4-carboxy-4-(nonanoylamino)butanoyl)/K30R-GLP-2(1-33); L17K((S)-4-carboxy-4-(decanoylamino)butanoyl)/K30R-GLP-2(1-33); L17K((S)-4-carboxy-4-(undecanoylamino)butanoyl)/K30R-GLP-2(1-33); L17K((S)-4-carboxy-4-(dodecanoylamino)butanoyl)/K30R-GLP-2(1-33); L17K((S)-4-carboxy-4-(tridecanoylamino)butanoyl)/K30R-GLP-2(1-33); L17K((S)-4-carboxy-4-(tetradecanoylamino)butanoyl)/K30R-GLP-2(1-33); L17K((S)-4-carboxy-4-(pentadecanoylamino)butanoyl)/K30R-GLP-2(1-33); L17K((S)-4-carboxy-4-(hexadecanoylamino)butanoyl)/K30R-GLP-2(1-33); L17K((S)-4-carboxy-4-(heptadecanoylamino)butanoyl)/K30R-GLP-2(1-33); L17K((S)-4-carboxy-4-(octadecanoylamino)butanoyl)/K30R-GLP-2(1-33); L17K((S)-4-carboxy-4-(nonadecanoylamino)butanoyl)/K30R-GLP-2(1-33); L17K((S)-4-carboxy-4-(eicosanoylamino)butanoyl)/K30R-GLP-2(1-33); L17K(4-(octanoylamino)butanoyl)/K30R-GLP-2(1-33); L17K(4-(nonanoylamino)butanoyl)/K30R-GLP-2(1-33); L17K(4-(decanoylamino)butanoyl)/K30R-GLP-2(1-33); L17K(4-(undecanoylamino)butanoyl)/K30R-GLP-2(1-33); L17K(4-(dodecanoylamino)butanoyl)/K30R-GLP-2(1-33); L17K(4-(tridecanoylamino)butanoyl)/K30R-GLP-2(1-33); L17K(4-(tetradecanoylamino)butanoyl)/K30R-GLP-2(1-33); L17K(4-(pentadecanoylamino)butanoyl)/K30R-GLP-2(1-33); L17K(4-(hexadecanoylamino)butanoyl)/K30R-GLP-2(1-33); L17K(4-(heptadecanoylamino)butanoyl)/K30R-GLP-2(1-33); L17K(4-(octadecanoylamino)butanoyl)/K30R-GLP-2(1-33); L17K(4-(nonadecanoylamino)butanoyl)/K30R-GLP-2(1-33); L17K(4-(eicosanoylamino)butanoyl)/K30R-GLP-2(1-33); A18K(3-(hexadecanoylamino)propionyl)/K30R-GLP-2(1-33); D21 K(3-(hexadecanoylamino)propionyl)/K30R-GLP-2(1-33); N24K(3-(hexadecanoylamino)propionyl)/K30R-GLP-2(1-33); Q28K(3-(hexadecanoylamino)propionyl)/K30R-GLP-2(1-33); D3E/S5K(3-(hexadecanoylamino)propionyl)/K30R/D33E-GLP-2(1-33); D3E/S7K(3-(hexadecanoylamino)propionyl)/K30R/D33E-GLP-2(1-33); D3E/D8K(3-(hexadecanoylamino)propionyl)/K30R/D33E-GLP-2(1-33); D3E/E9K(3-(hexadecanoylamino)propionyl)/K30R/D33E-GLP-2(1-33); D3E/M10K(3-(hexadecanoylamino)propionyl)/K30R/D33E-GLP-2(1-33); D3E/N11 K(3-(hexadecanoylamino)propionyl)/K30R/D33E-GLP-2(1-33); D3E/T12K(3-(hexadecanoylamino)propionyl)/K30R/D33E-GLP-2(1-33); D3E/I13K(3-(hexadecanoylamino)propionyl)/K30R/D33E-GLP-2(1-33); D3E/L14K(3-(hexadecanoylamino)propionyl)/K30R/D33E-GLP-2(1-33); D3E/D15K(3-(hexadecanoylamino)propionyl)/K30R/D33E-GLP-2(1-33); D3E/N16K(3-(hexadecanoylamino)propionyl)/K30R/D33E-GLP-2(1-33); D3E/L17K(3-(octanoylamino)propionyl)/K30R/D33E-GLP-2(1-33); D3E/L17K(3-(nonanoylamino)propionyl)/K30R/D33E-GLP-2(1-33); D3E/L17K(3-(decanoylamino)propionyl)/K30R/D33E-GLP-2(1-33); D3E/L17K(3-(undecanoylamino)propionyl)/K30R/D33E-GLP-2(1-33); D3E/L17K(3-(dodecanoylamino)propionyl)/K30R/D33E-GLP-2(1-33); D3E/L17K(3-(tridecanoylamino)propionyl)/K30R/D33E-GLP-2(1-33); D3E/L17K(3-(tetradecanoylamino)propionyl)/K30R/D33E-GLP-2(1-33); D3E/L17K(3-(pentadecanoylamino)propionyl)/K30R/D33E-GLP-2(1-33); D3E/L17K(3-(hexadecanoylamino)propionyl)/K30R/D33E-GLP-2(1-33); D3E/L17K(3-(heptadecanoylamino)propionyl)/K30R/D33E-GLP-2(1-33); D3E/L17K(3-(octadecanoylamino)propionyl)/K30R/D33E-GLP-2(1-33); D3E/L17K(3-(nonadecanoylamino)propionyl)/K30R/D33E-GLP-2(1-33); D3E/L17K(3-(eicosanoylamino)propionyl)/K30R/D33E-GLP-2(1-33); D3E/L17K((S)-4-carboxy-4-(octanoylamino)butanoyl)/K30R/D33E-GLP-2(1-33); D3E/L17K((S)-4-carboxy-4-(nonanoylamino)butanoyl)/K30R/D33E-GLP-2(1-33); D3E/L17K((S)-4-carboxy-4-(decanoylamino)butanoyl)/K30R/D33E-GLP-2(1-33); D3E/L17K((S)-4-carboxy-4-(undecanoylamino)butanoyl)/K30R/D33E-GLP-2(1-33); D3E/L17K((S)-4-carboxy-4-(dodecanoylamino)butanoyl)/K30R/D33E-GLP-2(1-33); D3E/L17K((S)-4-carboxy-4-(tridecanoylamino)butanoyl)/K30R/D33E-GLP-2(1-33); D3E/L17K((S)-4-carboxy-4-(tetradecanoylamino)butanoyl)/K30R/D33E-GLP-2(1-33); D3E/L17K((S)-4-carboxy-4-(pentadecanoylamino)butanoyl)/K30R/D33E-GLP-2(1-33); D3E/L17K((S)-4-carboxy-4-(hexadecanoylamino)butanoyl)/K30R/D33E-GLP-2(1-33); D3E/L17K((S)-4-carboxy-4-(heptadecanoylamino)butanoyl)/K30R/D33E-GLP-2(1-33); D3E/L17K((S)-4-carboxy-4-(octadecanoylamino)butanoyl)/K30R/D33E-GLP-2(1-33); D3E/L17K((S)-4-carboxy-4-(nonadecanoylamino)butanoyl)/K30R/D33E-GLP-2(1-33); D3E/L17K((S)-4-carboxy-4-(eicosanoylamino)butanoyl)/K30R/D33E-GLP-2(1-33); D3E/L17K(4-(octanoylamino)butanoyl)/K30R/D33E-GLP-2(1-33); D3E/L17K(4-(nonanoylamino)butanoyl)/K30R/D33E-GLP-2(1-33); D3E/L17K(4-(decanoylamino)butanoyl)/K30R/D33E-GLP-2(1-33); D3E/L17K(4-(undecanoylamino)butanoyl)/K30R/D33E-GLP-2(1-33); D3E/L17K(4-(dodecanoylamino)butanoyl)/K30R/D33E-GLP-2(1-33); D3E/L17K(4-(tridecanoylamino)butanoyl)/K30R/D33E-GLP-2(1-33); D3E/L17K(4-(tetradecanoylamino)butanoyl)/K30R/D33E-GLP-2(1-33); D3E/L17K(4-(pentadecanoylamino)butanoyl)/K30R/D33E-GLP-2(1-33); D3E/L17K(4-(hexadecanoylamino)butanoyl)/K30R/D33E-GLP-2(1-33); D3E/L17K(4-(heptadecanoylamino)butanoyl)/K30R/D33E-GLP-2(1-33); D3E/L17K(4-(octadecanoylamino)butanoyl)/K30R/D33E-GLP-2(1-33); D3E/L17K(4-(nonadecanoylamino)butanoyl)/K30R/D33E-GLP-2(1-33); D3E/L17K(4-(eicosanoylamino)butanoyl)/K30R/D33E-GLP-2(1-33); D3E/A18K(3-(hexadecanoylamino)propionyl)/K30R/D33E-G LP-2(1-33); D3E/D21 K(3-(hexadecanoylamino)propionyl)/K30R/D33E-GLP-2(1-33); D3E/N24K(3-(hexadecanoylamino)propionyl)/K30R/D33E-GLP-2(1-33); and D3E/Q28K(3-(hexadecanoylamino)propionyl)/K30R/D33E-GLP-2(1-33).

Methods for the preparation of GLP-2, analogs thereof as well as GLP-2 derivatives can be found in e.g. WO 99/43361 and WO 00/55119.

In a further embodiment of the invention the glucagon-like peptide is an insulinotropic analog of exendin-4(1-39), e.g. $Ser^2Asp^3$-exendin-4(1-39) wherein the amino acid residues in position 2 and 3 have been replaced with serine and aspartic acid, respectively (this particular analog also being known in the art as exendin-3).

In a further embodiment of the invention the glucagon-like peptide is an exendin-4 derivative wherein the substituent introduced is selected from amides, carbohydrates, alkyl groups, esters and lipophilic substituents. An example of an insulinotropic derivatives of exendin-4(1-39) and analogs thereof is $Tyr^{31}$-exendin-4(1-31)-amide.

In another embodiment of the invention the glucagon-like peptide is a stable exendin-4 compound. In another embodiment of the invention the glucagon-like peptide is a DPP-IV protected exendin-4 compound. In another embodiment of the invention the glucagon-like peptide is an immunomodulated exendin-4 compound.

Methods for the preparation of exendin-4, analogs thereof as well as exendin-4 derivatives can be found in e.g. WO 99/43708, WO 00/41546 and WO 00/55119.

The parent glucagon-like peptide can be produced by peptide synthesis, e.g. solid phase peptide synthesis using Fmoc- or Boc-chemistry or other well established techniques. The parent glucagon-like peptide can also be produced by a method which comprises culturing a host cell containing a DNA sequence encoding the polypeptide and capable of expressing the polypeptide in a suitable nutrient medium under conditions permitting the expression of the peptide, after which the resulting peptide is recovered from the culture.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The peptide produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gel filtration chromatography, affinity chromatography, or the like, dependent on the type of peptide in question.

The DNA sequence encoding the parent peptide may suitably be of genomic or cDNA origin, for instance obtained by preparing a genomic or cDNA library and screening for DNA sequences coding for all or part of the peptide by hybridisation using synthetic oligonucleotide probes in accordance with standard techniques (see, for example, Sambrook, J, Fritsch, E F and Maniatis, T, Molecular Cloning: A Laboratory Manual, Cold Spring Harbor Laboratory Press, New York, 1989). The DNA sequence encoding the peptide may also be prepared synthetically by established standard methods, e.g. the phosphoamidite method described by Beaucage and Caruthers, Tetrahedron Letters 22 (1981), 1859-1869, or the method described by Matthes et al., EMBO Journal 3 (1984), 801-805. The DNA sequence may also be prepared by polymerase chain reaction using specific primers, for instance as described in U.S. Pat. No. 4,683,202 or Saiki et al., Science 239 (1988), 487-491. The DNA sequence may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the peptide is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the peptide of the invention in a variety of host cells are well known in the art, cf. for instance Sambrook et al., supra.

The DNA sequence encoding the peptide may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

The vector may also comprise a selectable marker, e.g. a gene the product of which complements a defect in the host cell or one which confers resistance to a drug, e.g. ampicillin, kanamycin, tetracyclin, chloramphenicol, neomycin, hygromycin or methotrexate.

To direct a parent peptide of the present invention into the secretory pathway of the host cells, a secretory signal sequence (also known as a leader sequence, prepro sequence or pre sequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that normally associated with the peptide or may be from a gene encoding another secreted protein.

The procedures used to ligate the DNA sequences coding for the present peptide, the promoter and optionally the terminator and/or secretory signal sequence, respectively, and to insert them into suitable vectors containing the information necessary for replication, are well known to persons skilled in the art (cf., for instance, Sambrook et al., supra).

The host cell into which the DNA sequence or the recombinant vector is introduced may be any cell which is capable of producing the present peptide and includes bacteria, yeast, fungi and higher eukaryotic cells. Examples of suitable host cells well known and used in the art are, without limitation, *E. coli, Saccharomyces cerevisiae*, or mammalian BHK or CHO cell lines.

Pharmaceutical compositions containing a glucagon-like peptide purified according to the present invention typically contain various pharmaceutical excipients, such as preservatives, isotonic agents and surfactants. The preparation of pharmaceutical compositions is well-known to the skilled person. For convenience reference is made to Remington: *The Science and Practice of Pharmacy*, 19$^{th}$ edition, 1995.

Pharmaceutical compositions containing a glucagon-like peptide purified according to the present invention may be administered parenterally to patients in need of such treatment. Parenteral administration may be performed by subcutaneous injection, intramuscular injection, or intraveneous injection by means of a syringe, optionally a pen-like syringe. Alternatively administration can be performed by infusion, e.g. by use of an infusion pump.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLES

Example 1

Arg$^{34}$GLP-1$_{(7-37)}$ was expressed in yeast (*S. cerevisiae*) by conventional recombinant technology as described elsewhere (WO 98/08871). Arg$^{34}$GLP-1$_{(7-37)}$ in the fermentation broth was then purified by conventional reversed phase chromatography and subsequently precipitated at the isoelectric pH of the peptide, i.e. at pH 5.4. The precipitate was isolated by centrifugation. Following another RP-LC purification step and isoelectric precipitation, the Arg$^{34}$GLP-1$_{(7-37)}$ peptide was acylated as decribed in WO 00/55119 to give the GLP-1 derivative Arg$^{34}$Lys$^{26}$N$^{\epsilon}$(γ-Glu(N$^{\alpha}$-hexadecanoyl))GLP-1$_{(7-37)}$.

A mixture of 0.5 g/L Arg$^{34}$Lys$^{26}$N$^{\epsilon}$(γ-Glu(N$^{\alpha}$-hexadecanoyl))GLP-1$_{(7-37)}$ at pH 8.0 was prepared. The purity of the polypeptide was approx. 90% (approx. 5% D-His variant, D-His$^{7}$Arg$^{34}$Lys$^{26}$N$^{\epsilon}$(γ-Glu(N$^{\alpha}$-hexadecanoyl))GLP-1$_{(7-37)}$, where the histidine in position 7, i.e. the N-terminal of the peptide was racemized to a D-histidine residue, and 5% of other impurities). The mixture is purified using anion exchange chromatography.

0.005 column volume (CV) of the mixture was applied to a 1 mL Mono Q (Amersham Biosciences) anion exchanger column equilibrated with 10 CV 20 mM Tris-hydroxymethyl aminomethane, 63% (w/w) ethanol, pH 8.0. The column was washed with 3 CV equilibration solution, and the elution was performed with two linear salt gradients, the first gradient from 0-20 mM of NaCl, 20 mM Tris-hydroxymethyl aminomethane, 63% (w/w) ethanol, pH 8.0 over 20 CV, followed by the second gradient from 20-50 mM of NaCl, 20 mM Tris-hydroxymethyl aminomethane, 63% (w/w) ethanol, pH 8.0 over 10 CV. The flow was 40 CV/h and the temperature 25° C. throughout the experiment.

During the experiment the eluent from the column was fractionated and each of the fractions were analysed for the contents of D-His$^{7}$Arg$^{34}$Lys$^{26}$N$^{\epsilon}$(γ-Glu(N$^{\alpha}$-hexadecanoyl))GLP-1$_{(7-37)}$ and Arg$^{34}$Lys$^{26}$N$^{\epsilon}$(γ-Glu(N'-hexadecanoyl))GLP-1$_{(7-37)}$, respectively.

The data showed that the D-His variant of the peptide eluted before the Arg$^{34}$Lys$^{26}$N$^{\epsilon}$(γ-Glu(N$^{\alpha}$-hexadecanoyl))GLP-1$_{(7-37)}$, and the two forms of the peptide could thus be separated.

Example 2

A mixture of 2.0 g/L (γ-Glu(N$^{\alpha}$-hexadecanoyl))GLP-1$_{(7-37)}$ at pH 8 was prepared as described in example 1.

0.6 CV of the mixture was applied to a 4.7 mL Poros 20HQ (Perseptive Biosystems) anion exchanger column equilibrated with 5 CV 20 mM Tris-hydroxymethyl amino-methane, 63% (w/w) ethanol, pH 8.0. The column was washed with 6 CV equilibration solution, and the elution was performed with two linear salt gradients, the first gradient from 0-50 mM of NaCl, 20 mM Tris-hydroxymethyl amino-methane, 63% (w/w) ethanol, pH 8.0 over 12 CV, followed by the second gradient from 50-80 mM of NaCl, 20 mM Tris-hydroxymethyl amino-methane, 63% (w/w) ethanol, pH 8.0 over 20 CV. The flow was 90 CV/h and the temperature 40° C. throughout the experiment.

During the experiment the eluent from the column was fractionated and each of the fractions were analysed for the contents of D-His$^{7}$Arg$^{34}$Lys$^{26}$N$^{\epsilon}$(γ-Glu(N$^{\alpha}$-hexadecanoyl))GLP-1$_{(7-37)}$ and Arg$^{34}$Lys$^{26}$N$^{\epsilon}$(γ-Glu(N$^{\alpha}$-hexadecanoyl))GLP-1$_{(7-37)}$, respectively.

The data showed that the D-His variant of the peptide eluted before the Arg$^{34}$Lys$^{26}$N$^{\epsilon}$(γ-Glu(N$^{\alpha}$-hexadecanoyl))GLP-1$_{(7-37)}$, and the two forms of the peptide could thus be separated.

Example 3

A mixture of 0.5 g/L Arg$^{34}$Lys$^{26}$N$^{\epsilon}$(γ-Glu(N$^{\alpha}$-hexadecanoyl))GLP-1$_{(7-37)}$ at pH 8.0 is prepared as described in example 1.

0.1 CV of the mixture is applied to a 1 mL Mono Q (Amersham Biosciences) anion exchanger column equilibrated with 10 CV 20 mM Tris-hydroxymethyl amino-methane, 63% (w/w) ethanol, pH 8.0. The column is washed with 3 CV equilibration solution, and the elution is performed with two linear salt gradients, the first gradient from 0-20 mM of NaCl, 20 mM HEPES, 63% (w/w) ethanol, pH 8.0 over 20 CV, followed by the second gradient from 20-50 mM of NaCl, 20 mM HEPES, 63% (w/w) ethanol, pH 8.0 over 10 CV. The flow is 20 CV/h and the temperature 25° C. throughout the experiment.

During the experiment the eluent from the column is fractionated and each of the fractions are analysed for the contents of D-His$^{7}$Arg$^{34}$Lys$^{26}$N$^{\epsilon}$(γ-Glu(N$^{\alpha}$-hexadecanoyl))GLP-1$_{(7-37)}$ and Arg$^{34}$Lys$^{26}$N$^{\epsilon}$(γ-Glu(N$^{\alpha}$-hexadecanoyl))GLP-1$_{(7-37)}$, respectively.

The data show that the D-His variant of the peptide elutes before the Arg$^{34}$Lys$^{26}$N$^{\epsilon}$(γ-Glu(N'-hexadecanoyl))GLP-1$_{(7-37)}$, and the two forms of the peptide can thus be separated.

Example 4

A mixture of 0.5 g/L Arg$^{34}$Lys$^{26}$ N$^{\epsilon}$(γ-Glu(N$^{\alpha}$-hexadecanoyl))GLP-1$_{(7-37)}$ at pH 8.0 is prepared as described in example 1.

0.1 CV of the mixture is applied to a 1 mL Mono Q (Amersham Biosciences) anion exchanger column equilibrated with 10 CV 20 mM Tris-hydroxymethyl amino-methane, 63% (w/w) ethanol, pH 8.0. The column is washed with 3 CV equilibration solution, and the elution is performed with two linear salt gradients, the first gradient from 0-20 mM of NaCl, 20 mM Tris-hydroxymethyl amino-methane, 63% (w/w) ethanol, pH 8.0 over 20 CV, followed by the second gradient from 20-50 mM of NaCl, 20 mM Tris-hydroxymethyl amino-methane, 63% (w/w) ethanol, pH 8.0 over 10 CV. The flow is 80 CV/h and the temperature 25° C. throughout the experiment.

During the experiment the eluent from the column is fractionated and each of the fractions are analysed for the contents of D-His$^7$Arg$^{34}$Lys$^{26}$N$^\epsilon$(γ-Glu(Na-hexadecanoyl)) GLP-1$_{(7-37)}$ and Arg$^{34}$Lys$^{26}$N$^\epsilon$(γ-Glu(N$^\alpha$-hexadecanoyl)) GLP-1$_{(7-37)}$, respectively.

The data show that the D-His variant of the peptide elutes before the Arg$^{34}$Lys$^{26}$N$^\epsilon$(γ-Glu(N$^\alpha$-hexadecanoyl)) GLP-1$_{(7-37)}$, and the two forms of the peptide can thus be separated.

Example 5

A mixture of 0.5 g/L Arg$^{34}$Lys$^{26}$N$^\epsilon$(γ-Glu(N-hexadecanoyl))GLP-1$_{(7-37)}$ at pH 8.0 is prepared as described in example 1.

0.1 CV of the mixture is applied to a 1 mL Mono Q (Amersham Biosciences) anion exchanger column equilibrated with 10 CV 20 mM Tris-hydroxymethyl amino-methane, 63% (w/w) ethanol, pH 8.0. The column is washed with 3 CV equilibration solution, and the elution was performed with two linear salt gradients, the first gradient from 0-20 mM of sodium acetate, 20 mM Tris-hydroxymethyl amino-methane, 63% (w/w) ethanol, pH 8.0 over 20 CV, followed by a second gradient from 20-50 mM of CH$_3$COOH, 20 mM Tris-hydroxymethyl amino-methane, 63% (w/w) ethanol, pH 8.0 over 10 CV. The flow is 40 CV/h and the temperature 25° C. throughout the experiment.

During the experiment the eluent from the column is fractionated and each of the fractions are analysed for the contents of D-His$^7$Arg$^{34}$Lys$^{26}$N$^\epsilon$(γ-Glu(N$^\alpha$-hexadecanoyl)) GLP-1$_{(7-37)}$ and Arg$^{34}$Lys$^{26}$N$^\epsilon$(γ-Glu(N$^\alpha$-hexadecanoyl)) GLP-1$_{(7-37)}$, respectively.

The data show that the D-His variant of the peptide elutes before the Arg$^{34}$Lys$^{26}$N$^\epsilon$(γ-Glu(N$^\alpha$-hexadecanoyl)) GLP-1$_{(7-37)}$, and the two forms of the peptide can thus be separated.

Example 6

A mixture of 0.5 g/L Arg$^{34}$Lys$^{26}$N$^\epsilon$(γ-Glu(N$^\alpha$-hexadecanoyl))GLP-1$_{(7-37)}$ at pH 8.0 was prepared as described in example 1.

0.1 CV of the mixture was applied to a 1 mL Mono Q (Amersham Biosciences) anion exchanger column equilibrated with 10 CV 20 mM Tris-hydroxymethyl amino-methane, 63% (w/w) ethanol, pH 8.0. The column was washed with 3 CV equilibration solution, and the elution was performed with two linear salt gradients, the first gradient from 0-10 mM of Na$_2$SO$_4$, 20 mM Tris-hydroxymethyl amino-methane, 63% (w/w) ethanol, pH 8.0 over 20 CV, followed by the second grafient from 10-25 mM of Na$_2$SO$_4$, 20 mM Tris-hydroxymethyl amino-methane, 63% (w/w) ethanol, pH 8.0 over 10 CV. The flow was 40 CV/h and the temperature 25° C. throughout the experiment.

During the experiment the eluent from the column was fractionated and each of the fractions were analysed for the contents of D-His$^7$Arg$^{34}$Lys$^{26}$N$^\epsilon$(γ-Glu(Na-hexadecanoyl)) GLP-1$_{(7-37)}$ and Arg$^{34}$Lys$^{26}$N$^\epsilon$(γ-Glu(N$^\alpha$-hexadecanoyl)) GLP-1$_{(7-37)}$, respectively.

The data showed that the D-His variant of the peptide eluted before the Arg$^{34}$Lys$^{26}$ N$^\epsilon$(γ-Glu(N$^\alpha$-hexadecanoyl)) GLP-1$_{(7-37)}$, and the two forms of the peptide could thus be separated.

Example 7

A mixture of 2.0 g/L (γ-Glu(N$^\alpha$-hexadecanoyl)) GLP-1$_{(7-37)}$ at pH 8 was prepared as described in example 1.

The sample was subsequently spiked with approximately one third D-His$^7$Arg$^{34}$Lys$^{26}$N$^\epsilon$(γ-Glu(N$^\alpha$-hexadecanoyl)) GLP-1$_{(7-37)}$.

0.015 column volume (CV) of the mixture was applied to a 1 mL Mono Q (Amersham Biosciences) anion exchanger column equilibrated with 5 CV 20 mM Tris-hydroxymethyl aminomethane, 63% (w/w) ethanol, pH 8.0. The elution was performed with two linear salt gradients, the first gradient from 0-20 mM of NaCl, 20 mM Tris-hydroxymethyl aminomethane, 63% (w/w) ethanol, pH 8.0 over 12 CV, followed by the second gradient from 20-50 mM of NaCl, 20 mM Tris-hydroxymethyl amino-methane, 63% (w/w) ethanol, pH 8.0 over 8 CV. The flow was 48 CV/h and the temperature 25° C. throughout the experiment. The chromatogram is shown in FIG. 1.

Example 8

A mixture of 4.5 g/L (γ-Glu(N$^\alpha$-hexadecanoyl)) GLP-1$_{(7-37)}$ at pH 8 was prepared as described in example 1.

0.7 CV of the mixture was applied to a 152 mL Source 30Q (Amersham Biosciences) anion exchanger column equilibrated with 6 CV 20 mM Tris-hydroxymethyl amino-methane, 63% (w/w) ethanol, pH 8.0 The column was washed with 2 CV equilibration solution, and the elution was performed with two linear salt gradients, the first gradient from 0-23 mM of NaCl, 20 mM Tris-hydroxymethyl amino-methane, 63% (w/w) ethanol, pH 8.0 over 12 CV, followed by the second gradient from 23-30 mM of NaCl, 20 mM Tris-hydroxymethyl amino-methane, 63% (w/w) ethanol, pH 8.0 over 20 CV. The flow was 20 CV/h and the temperature 25° C. throughout the experiment.

During the experiment the eluent from the column was fractionated and each of the fractions were analysed for the contents of D-His$^7$Arg$^{34}$Lys$^{26}$N$^\epsilon$(γ-Glu(N$^\alpha$-hexadecanoyl)) GLP-1$_{(7-37)}$ and Arg$^{34}$Lys$^{26}$N$^\epsilon$(γ-Glu(N'-hexadecanoyl)) GLP-1$_{(7-37)}$, respectively.

The data showed that the D-His variant of the peptide eluted before the Arg$^{34}$Lys$^{26}$N$^\epsilon$(γ-Glu(N$^\alpha$-hexadecanoyl)) GLP-1$_{(7-37)}$, and the two forms of the peptide could thus be separated.

Example 9

A mixture of 5.0 g/L (γ-Glu(N$^\alpha$-hexadecanoyl)) GLP-1$_{(7-37)}$ at pH 8 was prepared as described in example 1.

0.6 CV of the mixture was applied to a 11.8 mL Source 30Q (Amersham Biosciences) anion exchanger column equilibrated with 5 CV 20 mM Tris-hydroxymethyl amino-methane, 63% (w/w) ethanol, pH 7.5. The column was washed with 1 CV equilibration solution, and the elution was performed with two linear salt gradients, the first gradient from 0-20 mM of NaCl, 20 mM Tris-hydroxymethyl amino-methane, 63% (w/w) ethanol, pH 7.5 over 12 CV, followed by the second gradient from 20-40 mM of NaCl, 20 mM Tris-hydroxymethyl amino-methane, 63% (w/w) ethanol, pH 7.5 over 20 CV. The flow was 20 CV/h and the temperature 25° C. throughout the experiment.

During the experiment the eluent from the column was fractionated and each of the fractions were analysed for the contents of D-His$^7$Arg$^{34}$Lys$^{26}$N$^\epsilon$(γ-Glu(N$^\alpha$-hexadecanoyl)) GLP-1$_{(7-37)}$ and Arg$^{34}$Lys$^{26}$N$^\epsilon$(γ-Glu(N$^\alpha$-hexadecanoyl)) GLP-1$_{(7-37)}$, respectively.

The data showed that the D-His variant of the peptide eluted before the Arg$^{34}$Lys$^{26}$ N$^\epsilon$(γ-Glu(N$^\alpha$-hexadecanoyl)) GLP-1$_{(7-37)}$, and the two forms of the peptide could thus be separated.

Example 10

A mixture of 5.0 g/L (γ-Glu(N$^\alpha$-hexadecanoyl)) GLP-1$_{(7-37)}$ at pH 8 was prepared as described in example 1.

0.6 CV of the mixture was applied to a 11.8 mL Source 30Q (Amersham Biosciences) anion exchanger column equilibrated with 5 CV 20 mM Tris-hydroxymethyl amino-methane, 63% (w/w) ethanol, pH 7.0. The column was washed with 1 CV equilibration solution, and the elution was performed with two linear salt gradients, the first gradient from 0-15 mM of NaCl, 20 mM Tris-hydroxymethyl amino-methane, 63% (w/w) ethanol, pH 7.0 over 12 CV, followed by the second gradient from 15-40 mM of NaCl, 20 mM Tris-hydroxymethyl amino-methane, 63% (w/w) ethanol, pH 7.0 over 20 CV. The flow was 20 CV/h and the temperature 25° C. throughout the experiment.

During the experiment the eluent from the column was fractionated and each of the fractions were analysed for the contents of D-His$^7$Arg$^{34}$Lys$^{26}$N$^\epsilon$(γ-Glu(N$^\alpha$-hexadecanoyl)) GLP-1$_{(7-37)}$ and Arg$^{34}$Lys$^{26}$N$^\epsilon$(γ-Glu(N$^\alpha$-hexadecanoyl)) GLP-1$_{(7-37)}$, respectively.

The data showed that the D-His variant of the peptide eluted before the Arg$^{34}$Lys$^{26}$N$^\epsilon$(γ-Glu(N$^\alpha$-hexadecanoyl)) GLP-1$_{(7-37)}$, and the two forms of the peptide could thus be separated.

Example 11

A mixture of 5.0 g/L (γ-Glu(N$^\alpha$-hexadecanoyl))GLP-1$_{(7-37)}$ at pH 8 was prepared as described in example 1.

0.6 CV of the mixture was applied to a 11.8 mL Source 30Q (Amersham Biosciences) anion exchanger column equilibrated with 5 CV 20 mM Tris-hydroxymethyl amino-methane, 63% (w/w) ethanol, pH 8.5. The column was washed with 1 CV equilibration solution, and the elution was performed with two linear salt gradients, the first gradient from 0-20 mM of NaCl, 20 mM Tris-hydroxymethyl amino-methane, 63% (w/w) ethanol, pH 8.5 over 12 CV, followed by the second gradient from 20-40 mM of NaCl, 20 mM Tris-hydroxymethyl amino-methane, 63% (w/w) ethanol, pH 8.5 over 20 CV. The flow was 20 CV/h and the temperature 25° C. throughout the experiment.

During the experiment the eluent from the column was fractionated and each of the fractions were analysed for the contents of D-His$^7$Arg$^{34}$Lys$^{26}$N$^\epsilon$(γ-Glu(N$^\alpha$-hexadecanoyl)) GLP-1$_{(7-37)}$ and Arg$^{34}$Lys$^{26}$N$^\epsilon$(γ-Glu(N$^\alpha$-hexadecanoyl)) GLP-1$_{(7-37)}$, respectively.

The data showed that the D-His variant of the peptide eluted before the Arg$^{34}$Lys$^{26}$N$^{\epsilon(\gamma\text{-}Glu(N\alpha)}$-hexadecanoyl)) GLP-1$_{(7-37)}$, and the two forms of the peptide could thus be separated.

Example 12

L-His$^1$-Exendin-4 and D-His$^1$-Exendin-4 was prepared by solid phase synthesis. A mixture of the two was prepared by dissolving the peptides in 10 mM Tris-hydroxymethyl amino-methane at pH 9.2 to a concentration of 1 g/L 1 CV of this mixture was loaded to a 1 ml mono-Q (Amersham Biosciences) anion exchange column equilibrated with 10CV 10 mM Tris-hydroxymethyl amino-methane, 63% (w/w) ethanol, pH 7.0. The column was washed with 1 CV 10 mM Tris-hydroxymethyl amino-methane, 63% (w/w) ethanol, pH 7.0, and the elution was performed isocratically with 10 mM Tris-hydroxymethyl amino-methane, 63% (w/w) ethanol, pH 7.0 over 20CV. The flow was 138 CV/h and the temperature was 25° C. throughout the experiment.

The elution (FIG. 3) showed that the L-His form of Exendin-4 eluted earlier than the D-his form of Exendin-4, and the two forms of the peptide could thus be separated.

Example 13

L17K, K30R-GLP2$_{(1-33)}$ was expressed in yeast (*S. cerevisiae*) by conventional recombinant technology in a similar manner as described in WO 98/08871 for GLP-1 peptides. L17K, K30R-GLP2$_{(1-33)}$ in the fermentation broth was then purified by conventional aniaon exchange and reversed phase chromatography and subsequently precipitated at the isoelectric pH of the peptide, i.e. at pH 4. The precipitate was isolated by centrifugation. D-His-L17K, K30R-GLP2$_{(1-33)}$ was prepared by solid phase synthesis.

A mixture of the two was prepared by dissolving the peptides in 10 mM Tris-hydroxymethyl amino-methane at pH 9.2 to a concentration of 1 g/L 1 CV of this mixture was loaded to a 1 ml mono-Q (Amersham Biosciences) anion exchange column equilibrated with 5CV 20 mM Tris-hydroxymethyl amino-methane, 63% (w/w) ethanol, pH 7.0. The column was washed with 1 CV 20 mM Tris-hydroxymethyl amino-methane, 63% (w/w) ethanol, pH 7.0, and the elution was as a gradient over 20 CV from 0 til 63 mM NaCl in 20 mM Tris-hydroxymethyl amino-methane, 63% (w/w) ethanol, at pH 7.0. The flow was 138 CV/h and the temperature was 25° C. throughout the experiment.

The elution showed that the D-His form of L17K, K30R-GLP2$_{(1-33)}$ eluted earlier than the L-his form of L17K, K30R-GLP2$_{(1-33)}$, and the two forms of the peptide could thus be separated.

The invention claimed is:

1. A method for separating two forms of a polypeptide having a single amino acid racemization, wherein the two polypeptides are A(X) and A(X*) where X is an L-amino acid, A(X) is a polypeptide comprising the amino acid X, X* is the D-isomer of X, A(X*) is a polypeptide comprising the amino acid X* but otherwise identical to A(X), said method comprising eluting the two forms of the polypeptide from an ion exchange chromatography resin under conditions where the salt concentration is increased at a pH that is no more than 1 pH unit from a pKa of X.

2. A method according to claim 1, wherein said method is for separating said polypeptides in preparative scale.

3. A method according to claim 1, wherein elution is performed at a pH which is substantially the same as the pH used for binding.

4. A method according to claim 1, wherein binding of the polypeptides is performed at a pH which is no more than about 5 pH from a pKa of the racemized amino acid residue under the conditions of elution.

5. A method according to claim 1, wherein said elution is performed at a pH which is higher than the isoelectric point of said polypeptides.

6. A method according to claim 1, wherein said polypeptide has a molecular weight of less than about 10 kDa.

7. A method according to claim 1, wherein the eluent comprises an organic modifier.

8. A method according to claim 1, wherein the eluent comprises an organic modifier in a concentration sufficient to keep said polypeptides soluble.

9. A method according to claim 7, wherein said organic modifier is ethanol.

10. A method according to claim 7, wherein said organic modifier is 2-propanol.

11. A method according to claim 7, wherein said organic modifier is acetonitrile.

12. A method according to claim 7, wherein said organic modifier is selected from the group consisting of methanol, 1-propanol and hexylene glycol.

13. A method according to claim 7, wherein the concentration of said organic modifier is from about 10% to about 80.

14. A method according to claim 1, wherein said salt is selected from the group consisting of sodium chloride, sodium sulphate, sodium acetate, potassium chloride, potassium sulphate, and potassium acetate.

15. A method according to claim 1, wherein the racemized amino acid residue is the N-terminal or the C-terminal amino acid residue.

16. A method according to claim 1, wherein the racemized amino acid residue is L-histidine.

17. A method according to claim 1, wherein the racemized amino acid residue is an amino acid analogue of histidine.

18. A method according to claim 17, wherein the racemized amino acid residue is selected from the group consisting of desamino-histidine, 2-amino-histidine, β-hydroxy-histidine, homohistidine, α-fluoromethyl-histidine and α-methyl-histidine.

19. A method according to claim 16, wherein the racemized amino acid residue is the N-terminal amino acid residue.

20. method according to claim 1, wherein the racemized amino acid residue is L-phenylalalnine.

21. A method according to claim 1, wherein said polypeptide is a glucagon-like peptide.

22. method according to claim 1, wherein said polypeptide is glucagon, a glucagon analogue, a derivative of glucagon or a derivative of a glucagon analogue.

23. A method according to claim 21, wherein said polypeptide is glucagon-like peptide 1(GLP-1), a GLP-1 analogue, a derivative of GLP-1 or a derivative of a GLP-1 analogue.

24. A method according to claim 23, wherein said polypeptide is selected from the group consisting of $Arg^{34}$-GLP-1(7-37), $Gly^8$-GLP-1(7-36)-amide, $Gly^8$-GLP-1(7-37), $Val^8$-GLP-1(7-36)-amide, $Val^8$GLP-1(7-37), $Val^8Asp^{22}$-GLP-1(7-36)-amide, $Val^8Asp^{22}$GLP-1(7-37), $Val^{8Glu22}$-GLP-1(7-36)-amide, $Val^8Glu^{22}$GLP-1(7-37), $Val^8Lys^{22}$-GLP-1(7-36)-amide, $Val^8Lys^{22}$-GLP-1(7-37), $Val^8Arg^{22}$-GLP-1-(7-36)-amide, $Val^8Arg^{22}$-GLP-1(7-37), $Val^8His^{22}$-GLP-1(7-36)-amide, $Val^8His^{22}$-GLP-1(7-37), $Val^8Trp^{19}Glu^{22}$-GLP-1(7-37), $Val^8Glu^{22}Val^{25}$-GLP-1(7-37), $Val^8Tyr^{16}Glu^{22}$-GLP-1(7-37), $Val^8Trp^{16}Glu^{22}$-GLP-1(7-37), $Val^8Leu^{16}Glu^{22}$-GLP-1(7-37), $Val^8Tyr^{18}Glu^{22}$-GLP-1(7-37), $Val^8Glu^{22}His^{37}$-GLP-1(7-37), $Val^8Glu^{22}Ile^{33}$-GLP-1(7-37), $Val^8Trp^{16}Glu^{22}Val^{25}Ile^{33}$-GLP-1(7-37), $Val^8Trp^{16}Glu^{22}Ile^{33}$-GLP-1(7-37), $Val^8Glu^{22}Val^{25}Ile^{33}$-GLP-1(7-37), $Val^8Trp^{16}Glu^{22}Val^{25}$-GLP-1(7-37), and derivatives of any of the foregoing polypeptides.

25. A method according to claim 23, wherein said derivative of GLP-1 or a derivative of a GLP-1 analogue has a lysine residue wherein a lipophilic substituent optionally via a spacer is attached to the epsilon amino group of said lysine.

26. A method according to claim 25, wherein said lipophilic substituent has from 8 to 40 carbon atoms.

27. A method according to claim 25, wherein said spacer is present and is selected from an amino acid.

28. A method according to claim 21, wherein said glucagon-like peptide is a dipeptidyl peptidase IV (DPPIV)-protected glucagon-like peptide.

29. A method according to claim 21, wherein said glucagon-like peptide is a plasma stable glucagon-like peptide.

30. A method according to claim 23, derivative of a GLP-1 analogue is $Arg^{34}$, $Lys^{26}(N^\epsilon$-(γ-Glu(Nα-hexadecanoyl)))-GLP-1(7-37).

31. A method according to claim 21, wherein said glucagon-like peptide has from 22 to 40 amino acid residues.

32. A method according to claim 21, wherein said glucagon-like peptide is glucagon-like peptide 2(GLP-2), a GLP-2 analogue, a derivative of GLP-2 or derivative of a GLP-2 analogue.

33. A method according to claim 32, wherein said derivative of GLP-2 or a derivative of a GLP-2 analogue has a lysine residue wherein a lipophilic substituent optionally via a spacer is attached to the epsilon amino group of said lysine.

34. A method according to claim 33, wherein said lipophilic substituent has from 8 to 40 carbon atoms.

35. A method according to claim 33, wherein said spacer is present and is an amino acid.

36. A method according to claim 32, wherein said glucagon-like peptide has from 27 to 39 amino acid residues.

37. A method according to claim 32, wherein said glucagon-like peptide is $Lys^{17}Arg^{30}$-GLP-2(1-33) or $Arg^{30}Lys^{17}N^\epsilon$(β-Ala($N^\alpha$-hexadecanoyyl)) GLP-2(1-33).

38. A method according to claim 32, wherein said glucagon-like peptide is $Gly^2$-GLP-2(1-33).

39. A method according to claim 21, wherein said glucagon-like peptide is exendin-4, an exendin-4 analogue, a derivative of exendin-4, derivative of an exendin-4 analogue.

40. A method according to claim 39, wherein said glucagon-like peptide is exendin-4.

41. A method according to claim 39, wherein said glucagon-like peptide is HGEGTFTSDLSKQMEEEAVR-LFIEWLKNGGPSSGAPPSKKKKKK-NH2 (SEQ ID NO:7).

42. A method according to claim 39, wherein said derivative of exendin-4 or derivative of an exendin-4 analogue is an acylated peptide or a pegylated peptide.

43. A method according to claim 39, wherein said derivative of exendin-4 or derivative of an exendin-4 analogue has a lysine residue wherein a lipophilic substituent optionally via a spacer is attached to the epsilon amino group of said lysine.

44. A method according to claim 43, wherein said lipophilic substituent has from 8 to 40 carbon atoms.

45. A method according to claim 43, wherein said spacer is present and is an amino acid.

46. A method according to claim 1, wherein said polypeptide is an insulin peptide.

47. A method according to claim 46, wherein said insulin peptide is human insulin, an analogue of human insulin, a derivative of human insulin or a derivative of a human insulin analogue.

48. A method according to claim 47, wherein said insulin peptide is human insulin.

49. A method according to claim 47, wherein said human insulin analogue is selected from the group consisting of $Asp^{B28}$-human insulin, $Lys^{B28}Pro^{B29}$-human insulin, $Lys^{B3}Glu^{B29}$-human insulin, $Gly^{A21}Arg^{B31}Arg^{B32}$-human insulin, and des(B30) human insulin.

50. A method according to claim 47, wherein said derivative of human insulin or said derivative of a human insulin analogue has a lysine residue wherein a lipophilic substituent optionally via a spacer is attached to the epsilon amino group of said lysine.

51. A method according to claim 50, wherein said lipophilic substituent has from 8 to 40 carbon atoms.

52. A method according to claim 50, wherein said spacer is present and is an amino acid.

53. A method according to claim 50, wherein said derivative of a human insulin analogue is $N^{\epsilon B29}$-tetadecanoyl des (B30) human insulin or $N^{\epsilon B29}$-litocholoyl-γ-glutamyl des (B30) human insulin.

54. A method according to claim 46, wherein the racemized amino acid residue is L-phenylalanine at position 1 in the B-chain of the insulin peptide.

55. A polypeptide product manufactured by a process comprising the steps of
   a) purifying a polypeptide using the method according to claim 1, and
   b) isolating said polypeptide to give the resulting polypeptide product.

56. A pharmaceutical composition prepared by a process comprising the steps of
   a) purifying a polypeptide using a method according to claim 1,
   b) drying said purified polypeptide, and
   c) admixing said dried polypeptide with a pharmaceutically acceptable excipient.

* * * * *

UNITED STATES PATENT AND TRADEMARK OFFICE
CERTIFICATE OF CORRECTION

| | |
|---|---|
| PATENT NO. | : 7,749,955 B2 |
| APPLICATION NO. | : 11/358676 |
| DATED | : July 6, 2010 |
| INVENTOR(S) | : Hansen et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 520 days.

In column 24, line 51, delete "5 pH" and insert --0.5 pH--.

In column 25, line 41, delete "$Val^8$ $^{Glu22}$" and insert --$Val^8$ $Glu^{22}$--.

In column 26, line 2, delete "(Nα-hexadecanoyl)" and insert --($N^\alpha$-hexadecanoyl)--.

In column 26, line 22, delete "hexadecanoyyl" and insert --hexadecanoyl--.

Signed and Sealed this

Twenty-sixth Day of October, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,749,955 B2 | Page 1 of 1 |
| APPLICATION NO. | : 11/358676 | |
| DATED | : July 6, 2010 | |
| INVENTOR(S) | : Hansen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 520 days.

Signed and Sealed this
Twenty-eighth Day of December, 2010

David J. Kappos
*Director of the United States Patent and Trademark Office*